(12) United States Patent
O'Day

(10) Patent No.: US 9,301,774 B2
(45) Date of Patent: Apr. 5, 2016

(54) LUMEN REENTRY MECHANISM AND METHOD

(71) Applicant: Therese J. O'Day, Bloomington, IN (US)

(72) Inventor: Therese J. O'Day, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 472 days.

(21) Appl. No.: 13/735,268

(22) Filed: Jan. 7, 2013

(65) Prior Publication Data

US 2014/0194913 A1  Jul. 10, 2014

(51) Int. Cl.
| A61B 17/32 | (2006.01) |
| A61B 17/3207 | (2006.01) |
| A61B 17/34 | (2006.01) |
| A61B 17/22 | (2006.01) |
| A61B 19/00 | (2006.01) |

(52) U.S. Cl.
CPC ......... *A61B 17/3207* (2013.01); *A61B 17/3478* (2013.01); *A61B 2017/22095* (2013.01); *A61B 2019/5466* (2013.01)

(58) Field of Classification Search
CPC .............. A61B 17/22; A61B 17/3207; A61B 2017/00252; A61B 17/11; A61B 17/0218; A61B 17/3478
See application file for complete search history.

(56) References Cited

U.S. PATENT DOCUMENTS

| 6,511,458 | B2 | 1/2003 | Milo et al. |
| 8,083,727 | B2 | 12/2011 | Kugler et al. |
| 8,172,863 | B2 | 5/2012 | Robinson et al. |
| 8,202,246 | B2 | 6/2012 | Kugler et al. |
| 8,241,311 | B2 | 8/2012 | Ward et al. |
| 2001/0047165 | A1 | 11/2001 | Makower et al. |
| 2006/0094930 | A1 | 5/2006 | Sparks et al. |
| 2006/0206125 | A1* | 9/2006 | Fogarty et al. ................ 606/159 |
| 2008/0243067 | A1 | 10/2008 | Rottenberg et al. |
| 2010/0063534 | A1 | 3/2010 | Kugler et al. |
| 2012/0136382 | A1 | 5/2012 | Kugler et al. |

OTHER PUBLICATIONS

Cordis Corporation, Outback® LTD® Re-Entry Catheter, 2pp., published on the World Wide Web prior to Oct. 18, 2012.
Bridgepoint, Stingray™ CTO Re-Entry System, 3pp., published on the World Wide Web prior to Oct. 18, 2012.

* cited by examiner

*Primary Examiner* — Victor Nguyen
(74) *Attorney, Agent, or Firm* — Lieil & McNeil

(57) ABSTRACT

A lumen reentry mechanism includes a catheter configured to bypass an area of stenosis, and having a longitudinal passage with a side hole. A piercing tool is positioned within the passage and has a transverse end section with a cutting tip, trapped between first and second longitudinally extending beads within the passage. Trapping of the piercing tool limits contact between the cutting tip and an inner surface of the catheter. Related methodology is also disclosed.

20 Claims, 5 Drawing Sheets

LUMEN REENTRY MECHANISM AND METHOD

TECHNICAL FIELD

The present disclosure relates generally to bypassing an area of stenosis in a vein or artery of a patient, and relates more particularly to limiting contact between a catheter and a cutting tip on a piercing tool advanced through the catheter to reenter a lumen of the vein or artery from a subintimal space.

BACKGROUND

A great many different interventional tools and techniques have been proposed over the years for treating narrowing, blockage, and other conditions of veins or arteries leading to insufficiency of blood flow. Endovascular techniques, as opposed to open surgery, are commonly used to minimize invasiveness of the procedure. A classic example is the percutaneous entry of a wire guide or the like into a vein or artery to be treated, followed by use of the wire guide to position a treatment device such as a stent, balloon, infusion catheter, or a variety of other mechanisms, at or near a location to be treated.

In navigating the circulatory system from a remote access site, wires, catheters and other interventional tools are commonly required to traverse a route having potentially numerous turns and junctions. Since an access site through a patient's skin can sometimes be as much as a meter or possibly even further from a target treatment location, a relatively high degree of skill and specialized tools are often required for successful access and treatment.

A given treatment location such as a narrowing or blockage as noted above, must often be crossed so that interventional tools can be successfully used at that location itself, or others further on. In some instances, wires can be used to push through a calcified lesion, fibrous thrombus cap or the like. In other instances, attempting to push a wire straight through may not be possible, or considered risky, due to the risk of puncturing the vascular wall. In such instances, clinicians may attempt to cross subintimally, via pushing a wire or the like through tissues forming the vascular wall, with the intention of reentering the true lumen of the vein or artery on the other side of the area bypassed.

A wide variety of different lumen reentry techniques have been proposed, some with a measure of success, such as a specialized deflectable hollow needle that punches its way from the subintimal layers back into the true lumen of the vein or artery, enabling a wire guide to navigate around a lesion with the eventual intention of forming a conduit for blood flow through the subintimal layers. U.S. Pat. No. 6,511,458 to Milo, et al, is directed to deflecting a wire advanced to a point distal to an occlusion back into a blood vessel lumen using a deflecting catheter advanced over the wire. After the wire is returned to the lumen, the catheter may be withdrawn and the wire is then available for introduction of other tools. Those skilled in the art will be familiar with the necessity of properly orienting a reentry tool such as that taught by Milo et al. For instance, if the catheter providing for delivery or placement of the reentry tool is not properly oriented, the tool might form a passage upon deployment out of the vein or artery, or through the subintimal tissues, rather than returning to the true lumen. Milo, et al appear to address this concern using a visualization subsystem of the catheter system, apparently some form of imaging or enhancement to imaging.

SUMMARY OF THE DISCLOSURE

In one aspect, a lumen reentry mechanism includes a catheter having an elongate tubular body for bypassing an area of stenosis in a vein or artery via a subintimal space. The elongate tubular body includes a proximal body end and a distal body end, and defines a longitudinal axis, a passage extending longitudinally between the proximal and distal body ends, and a side hole connecting with the passage. The elongate tubular body further has a first and a second bead extending longitudinally between the proximal body end and the side hole, and projecting into the passage. The mechanism further includes a piercing tool within the passage including a elongate proximal shaft section oriented substantially parallel to the longitudinal axis, and an attached distal end section oriented transverse to the elongate proximal shaft section. The distal end section has a cutting tip configured to exit the side hole for forming a reentry opening from the subintimal space to a lumen of the vein or artery. The piercing tool is slidable within the passage from a first position to an advanced position at which the cutting tip is in axial alignment with the side hole. The distal end section is trapped between the first and second beads such that contact between the cutting tip and the elongate tubular body is limited during the sliding of the piercing tool.

In another aspect, a method of bypassing an area of stenosis in a vein or artery in a patient includes advancing a catheter defining a longitudinal axis past the area of stenosis via a subintimal space in the vein or artery. The method further includes sliding a piercing tool having an elongate proximal shaft section and a transverse distal end section through a passage in the catheter to a position at which a cutting tip on the distal end section is in axial alignment with a side hole in the catheter connecting with the passage. The method further includes trapping the distal end section, during sliding the piercing tool, between a first and a second longitudinally extending bead projecting into the passage, such that contact between the cutting tip and the catheter is limited. The method still further includes forming a reentry opening from the subintimal space to a lumen of the vein or artery at least in part by advancing the distal end section out of the side hole such that the cutting tip pierces tissue forming a vascular wall defining the lumen.

In still another aspect, a lumen reentry mechanism includes a catheter having an elongate tubular body for bypassing an area of stenosis in a vein or artery via a subintimal space. The elongate tubular body has a proximal and a distal body end, and defines a longitudinal axis, a passage extending longitudinally between the proximal and distal body ends, and a side hole connecting with the passage. The elongate tubular body further has a first and a second bead extending longitudinally between the proximal body end and the side hole, and projecting into the passage. The mechanism further includes a piercing tool having an elongate proximal shaft section oriented substantially parallel to the longitudinal axis, and an attached distal end section oriented transverse to the elongate proximal shaft section and having a cutting tip configured to exit the side hole for forming a reentry opening from the subintimal space to a lumen of the vein or artery. The piercing tool is slidable within the passage from a first position to an advanced position at which the cutting tip is in axial alignment with the side hole, and such that the distal end section is trapped during the sliding between the first and second beads to limit contact between the cutting tip and the elongate tubular body.

DETAILED DESCRIPTION

Figure 1:
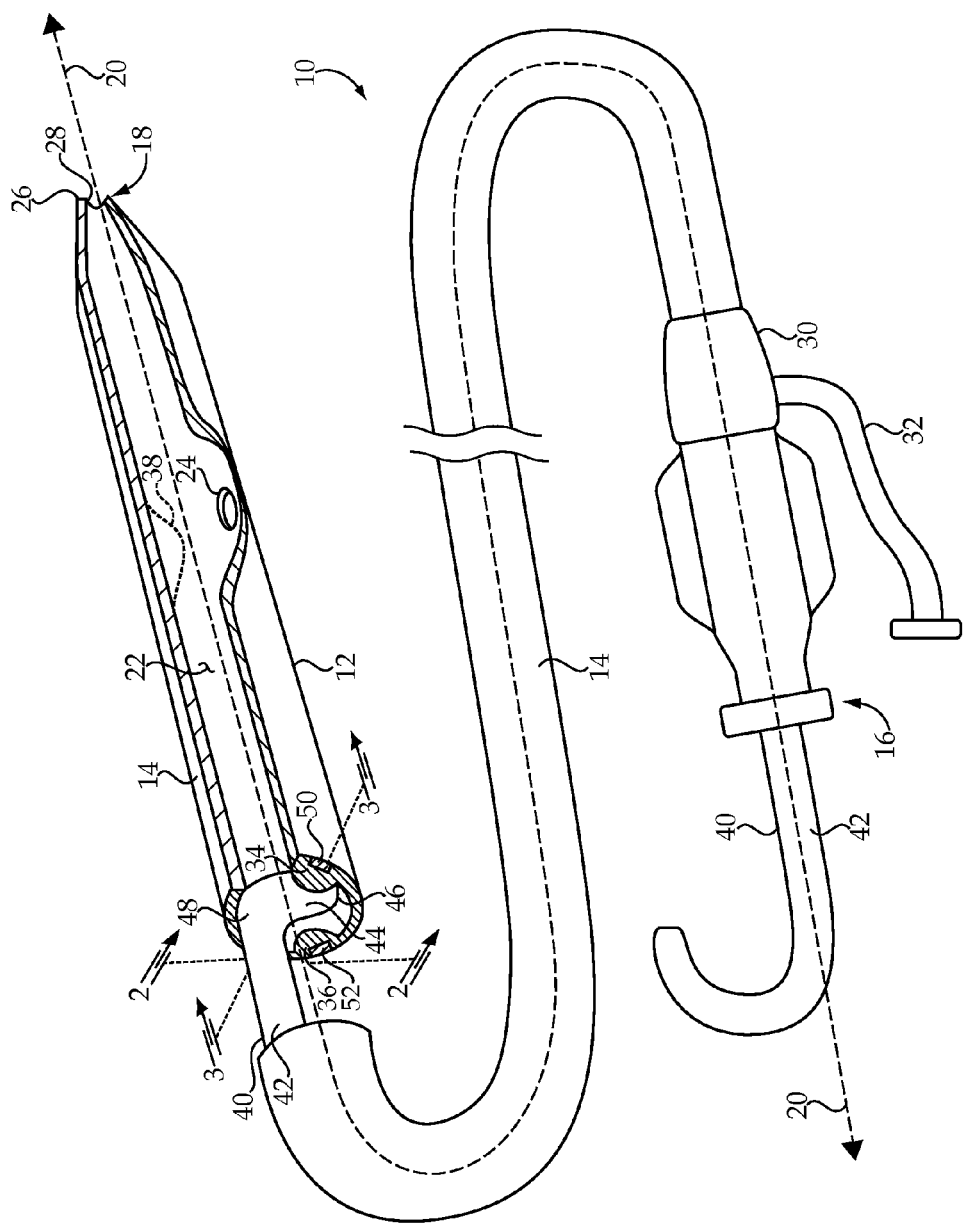
FIG. 1 is a partially sectioned side diagrammatic view, in multiple section planes, of a lumen reentry mechanism, according to one embodiment.

Referring to FIG. 1, there is shown a lumen reentry mechanism 10 according to one embodiment. Mechanism 10 includes a catheter 12 having an elongate tubular body 14 for bypassing an area of stenosis in a vein or artery via a subintimal space. Body 14 has a proximal body end 16 and a distal body end 18, and defines a longitudinal axis 20. Body 14 further defines a passage 22 extending longitudinally between proximal and distal body ends 16 and 18, and a side hole 24 connecting with passage 22. Distal end 18 includes a distal tip 26 having a tip opening 28 formed therein, for passing catheter 12 over a wire guide or the like in a manner further discussed herein. A manifold 30 may be positioned near proximal body end 16, and connects with a side arm 32 or the like configured for irrigation of passage 22, injection of contrast agent into a patient, or for still other known purposes. Body 14 may be formed as a one-piece extrusion, at least between manifold 30 and distal end 18, but could be assembled from multiple different pieces or formed via another technique in alternative strategies. As will be further apparent from the following description, mechanism 10 may be uniquely configured for bypassing an area of stenosis in an efficient and effective manner, and avoiding such problems as could arise from snagging, abrading, or otherwise contacting inner walls of body 14 forming passage 22 with other interventional tools.

Body 14 may further include a first bead 34 and a second bead 36 extending longitudinally between proximal body end 16 and distal body end 18, and projecting into passage 22. In FIG. 1, a portion of body 14 is shown in cut-away view making visible beads 34 and 36 in an axial section plane normal to axis 20. Other features of catheter 12 including side hole 24 and a protrusion 38 to be described later are visible via a longitudinal cut away, in two section planes. Mechanism 10 further includes a piercing tool 40 within passage 22 and including an elongate proximal shaft section 42 oriented substantially parallel to longitudinal axis 20, and an attached distal end section 44 oriented transverse to shaft section 42. Tool 40 may have the form of an elongate hollow cannula-like tool, wherein shaft section 42 adjoins distal end section 44 at a bend 48, the significance of which will be apparent from the following description. Tool 40 is slidable within passage 22 from a first position, approximately as shown in FIG. 1, to an advanced position at which cutting tip 46 is in axial alignment and in register with side hole 24. "Axial alignment" means positioned at the same position along axis 20. It should be understood that tool 40 may have a plurality of "first" positions, as any position in which tip 46 is not in axial alignment with side hole 24 could be thusly understood. Distal end section 44 is trapped between first and second beads 34 and 36 such that contact between cutting tip 46 and body 14 is limited during the sliding of tool 40.

Certain known lumen reentry mechanisms employ shape memory materials or the like to enable a device which punctures through a vascular wall to transition from a relatively linear delivery configuration to a curvilinear deployed configuration upon sliding the tool out of a delivery catheter. Other such mechanisms attempt to employ geometry of the delivery catheter itself to shape such a tool and direct the same during deployment. Mechanism 10 differs from such strategies, for reasons including the manner in which tool 40 is delivered through catheter 12. Rather than relying solely or even predominately upon geometry of a delivery catheter or shape memory of the piercing tool itself, piercing tool 40 is advanced through catheter 12 in a configuration similar or identical to the configuration considered suitable for performing its intended function, namely, forming a reentry opening through vascular tissue forming a wall of a true lumen in a vein or artery. While this general strategy has various advantages, it has been discovered that employing a piercing tool with a distal end section positioned at a fixed transverse orientation relative to a proximal shaft section can result in the cutting tip snagging, abrading, hanging up or otherwise interacting by way of contact with the catheter body itself. As noted above, trapping distal end section 44 between first and second beads 34 and 36 can minimize or eliminate such contact during sliding tool 40 for deployment. Minimizing or eliminating such contact has the desirable effect of ensuring tool 40 can be slid through catheter 12 as readily as practicable. In addition, the fixed configuration of tool 40 within body 14 enables the shape of tool 40 to itself be leveraged in imaging and properly orienting mechanism 10 for formation of a reentry opening as further discussed herein. To this end, catheter 12 may further include one or more radiopaque stripes attached to body 14 and extending longitudinally between proximal body end 16 and distal body end 18. In a practical implementation strategy, mechanism 10 includes a first radiopaque stripe 50 and a second radiopaque stripe 52.

Figure 2:
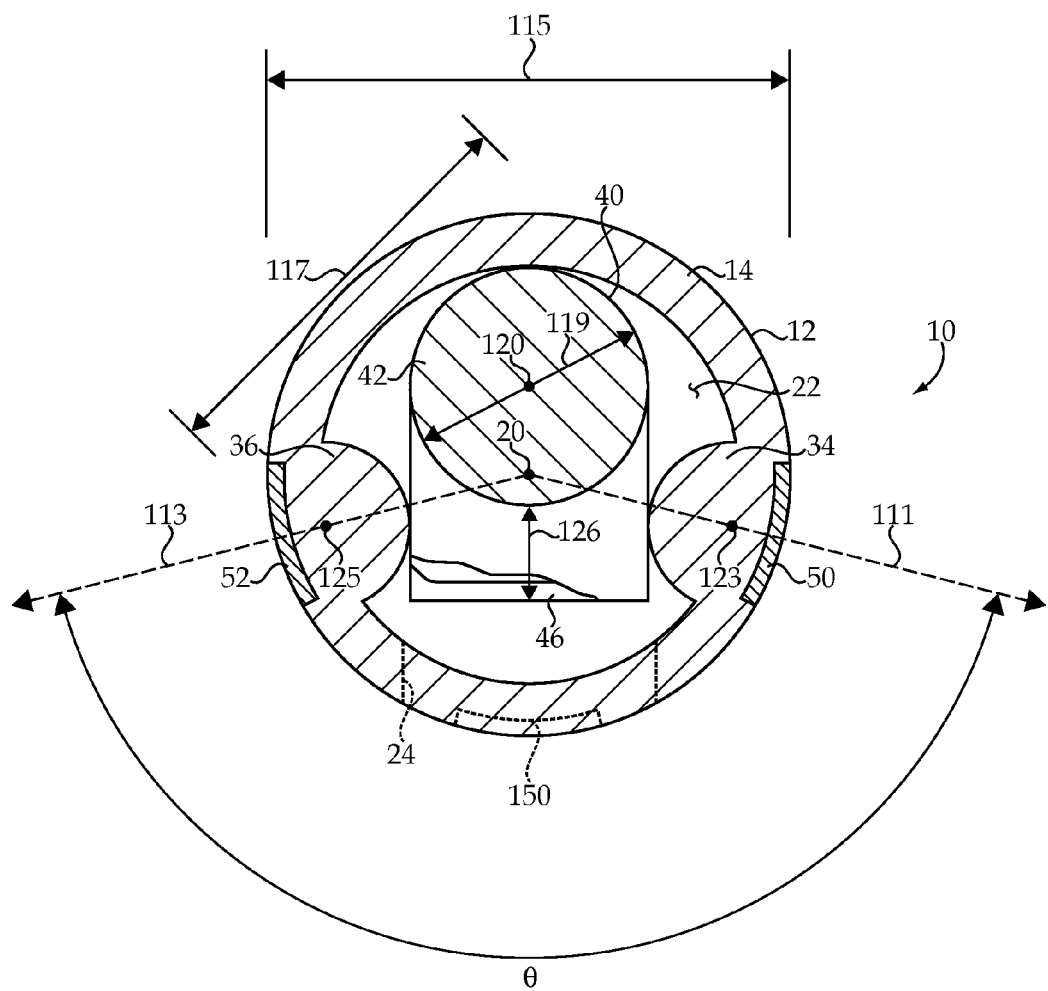
FIG. 2 is a sectioned view taken along line 2-2 of FIG. 1.

Referring also now to FIG. 2, there is shown a sectioned view taken along line 2-2 of FIG. 1. Tool 40 is shown trapped between beads 34 and 36, and in a practical implementation strategy will be in contact with at least one of first and second beads 34 and 36 and typically in contact with both. Trapping distal end section 44 as discussed herein may enable positioning of cutting tip 46 in register with side hole 24. First and second beads 34 and 36 may be oriented parallel to one another, although the present disclosure is certainly not thusly limited, and each have a rounded shape. The rounded shape may be a shape evident in the section plane of FIG. 2, and enables the contact with distal end section 44 to define a line pattern of contact, at least from the sliding of tool 40 through catheter 12. This should be understood to mean that points of contact between distal end section 44 and one or both of beads 34 and 36 may define a line, which would extend in and out of the page perpendicular to the section plane in FIG. 2. In the subject section plane, normal to axis 20, first and second beads 34 and 36 may each have a semi-circular cross-sectional shape. The corresponding semi-circles may have center points 123 and 125, respectively. First and second beads 34 and 36 may further be shaped such that a first longitudinal plane 111 bisects first bead 34, a second longitudinal plane 113 bisects second bead 36, and cutting tip 46 is positioned between first and second longitudinal planes 111 and 113.

Longitudinal axis 20 may lie at an intersection of first and second longitudinal planes 111 and 113, such that cutting tip 46 is positioned within an angle Θ defined by first and second longitudinal planes 111 and 113. Angle Θ may be less than 180°. More particularly, angle Θ may be from about 120° to about 160°, and more particularly still may be equal to about 156° in certain embodiments. As used herein, the term "about" should be understood in the context of rounding to a consistent number of significant digits. Accordingly, "about" 120° means from 115° to 124°, "about" 156° means from 155.5° to 156.4°, and so on. It will be further understood that a second angle defined by longitudinal planes 111 and 113, opposite angle Θ, will be greater than 180°. As noted above, each of beads 34 and 36 may have a semi-circular shape each defining a semi-circle having a center point 123 and 125, respectively. An arc radius defined by each of those semi-circles in the section plane of FIG. 2 may be about 0.01 inches or less in certain embodiments.

Other example dimensional features of catheter 12 include an outer diameter dimension 115 of body 14, equal to about 0.08 inches or less. An inner diameter dimension 117 of body 14 may be about 0.06 inches or less. Also shown in FIG. 2 is a second longitudinal axis 120 defined by proximal shaft section 42, and extending generally in parallel with but offset from longitudinal axis 20. Proximal shaft section 42 may have an outer diameter dimension 119 of about 0.03 inches or less. It will be noted that proximal shaft section 42 would be understood to generally extend in and out of the page in FIG. 2, and distal end section 44 would be understood to extend in an orthogonal direction. Proximal shaft and distal end sections 42 and 44 may be formed as one piece, with bend 48 transitioning therebetween, and defining a bend angle from about 45° to about 90°, though bend angles larger or smaller than this range are contemplated herein. Distal end section 44 may further have a length 121 extending from proximal shaft section 42 to cutting tip 46 which is about 0.03 inches or less.

Figure 10:
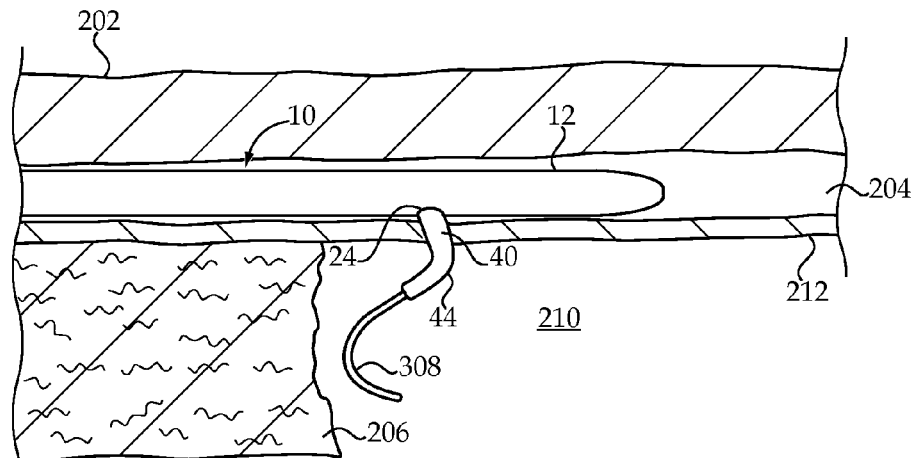
FIG. 10 is a side diagrammatic view at yet another stage of the procedure.

The example dimensional attributes set forth herein represent a practical implementation strategy. Features of mechanism 10 are nevertheless expected to proportionally scale. Accordingly, an analogous lumen re-entry mechanism having similar proportions to those of mechanism 10, but doubled, tripled or fractionally increased or decreased will likely still fall within the scope of the present disclosure. Radiopaque stripes 50 and 52 are also shown in FIG. 10. Suitable radiopaque materials may be co-extruded with nylon or another suitable elastomeric material from which catheter 12 is formed. Also shown in phantom in FIG. 2 is a radiopaque stripe 150, which might be used in combination with stripes 50 and 52 in mechanism 10, but could be independently used without stripes 50 and 52 in certain embodiments. In other words, while two stripes, bi-sected by longitudinal planes 111 and 113, respectively, provides a practical implementation strategy, a single radiopaque stripe positioned, for instance, approximately where stripe 150 is shown is also a viable strategy. The significance and example uses of radiopaque stripes in properly orienting mechanism 10 will be further apparent from the following description.

Figure 4:
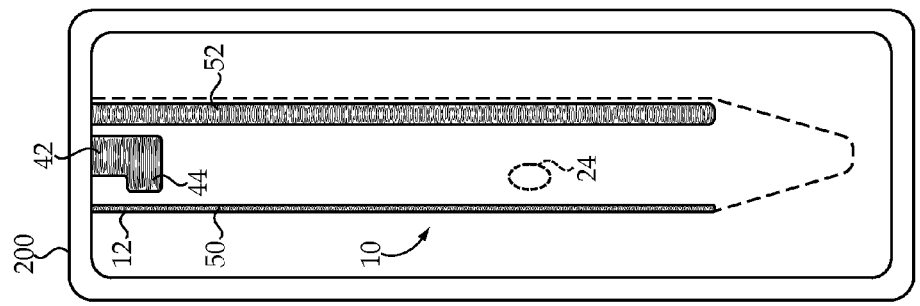
FIG. 4 is a diagrammatic view of an image of the lumen reentry mechanism of FIG. 1 at a first orientation.
Figure 3:
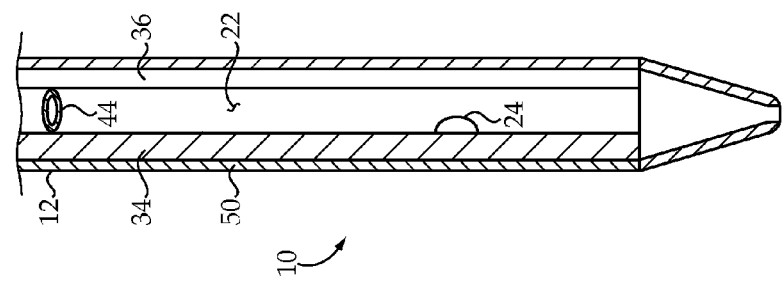
FIG. 3 is a sectioned view taken along line 3-3 of FIG. 1.

Referring also now to FIG. 3, there is shown a sectioned view taken along line 3-3 of FIG. 1. In FIG. 3 the section plane is passing through stripe 50 but above stripe 52, and also through bead 34 but above bead 36. Accordingly, stripe 50 and bead 34 are shown sectioned, while bead 36 is shown in elevation and stripe 52 is not visible. Referring also now to FIG. 4, there is shown an image of catheter 12 as it might appear on a conventional radiography imaging machine 200.

Figure 5:
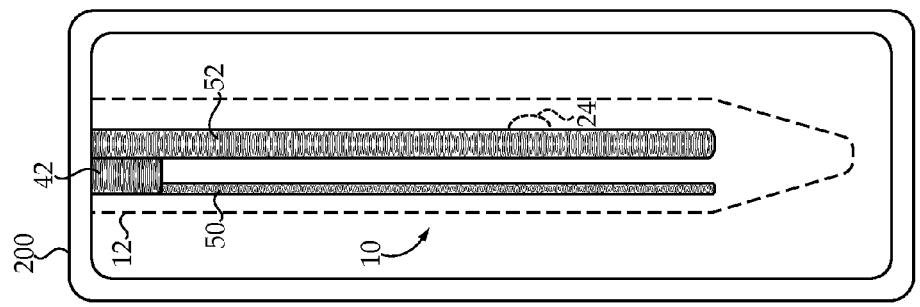
FIG. 5 is a diagrammatic view of an image of the lumen reentry mechanism of FIG. 1 at a second orientation.

In FIG. 4, mechanism 10 has approximately the same orientation as it does in FIG. 3. Accordingly, stripe 52 appears relatively wider and stripe 50 appears relatively narrower, while distal end section 44 is partially visible and shown descending into the page at an angle from part of proximal shaft section 42. Referring to FIG. 5, there is shown mechanism 10 having been rotated slightly to produce an image where stripe 52 is now obstructing distal end section 44, and proximal shaft section 42 is partly obstructing stripe 50. It may be noted that side hole 24 is positioned below stripe 52 and partially obstructed thereby, although side hole 24 might not of course be visible in an actual radiograph.

Figure 6:
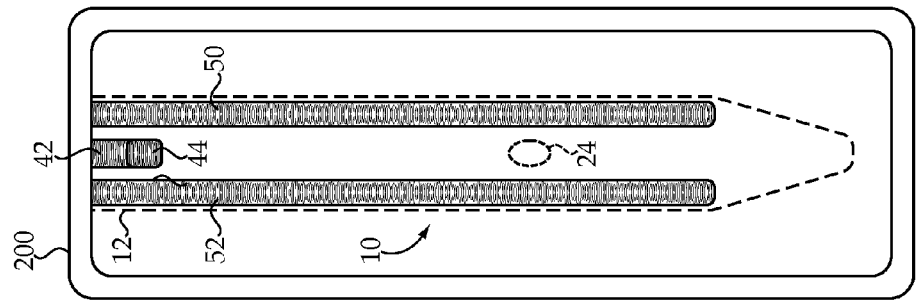
FIG. 6 is a diagrammatic view of an image of the lumen reentry mechanism of FIG. 1 at a third orientation.

Referring now to FIG. 6, there is shown mechanism 10 having been further rotated, such that stripes 52 and 50 are now positioned on left and right sides of distal end section 44 and proximal shaft section 42, respectively, such that distal end section 44 is generally pointed towards an observer in a direction out of the page. A clinician can exploit images produced by radiopaque parts of mechanism 10 to generally line up distal end section 44 and cutting tip 46 in a desired direction for forming a re-entry opening as further discussed herein. In the case a radiopaque stripe is positioned similar to stripe 150 in FIG. 2, a similar technique could be used to rotate and otherwise manipulate mechanism 10 to a position at which stripe 150 is lined up with distal end section 44 and proximal shaft section 42 in an imaging plane for analogous purposes.

INDUSTRIAL APPLICABILITY

Figure 7:
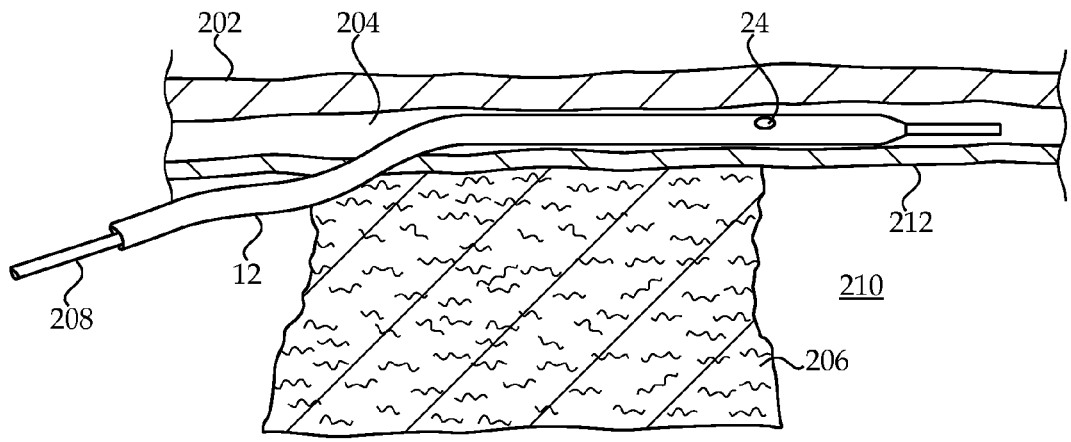
FIG. 7 is a side diagrammatic view at one stage of a procedure, according to one embodiment.

Referring now to FIG. 7, there is shown catheter 12 having been advanced past an occlusion 206 or the like in a vein or artery 202, through a subintimal space 204. In the embodiment shown, catheter 12 has been advanced over a wire guide 208 to a position at which side hole 24 is located past the occlusion 206. A true lumen 210 of the vein or artery 202 is separated from subintimal space 204 via tissue forming a vascular wall 212. It may be noted in FIG. 7 that side hole 24 generally faces out of the page, an orientation likely poorly suited for forming a re-entry opening in the present instance. A clinician can, via the use of imaging machine 200, and techniques analogous to those discussed in connection with FIGS. 2-6, rotate and manipulate catheter 12 to properly position side hole 24 for forming a re-entry opening. Such manipulation may take place where wire 208 extends through catheter 12, but may also take place where wire 208 has been removed, and substituted with tool 40.

Figure 8:
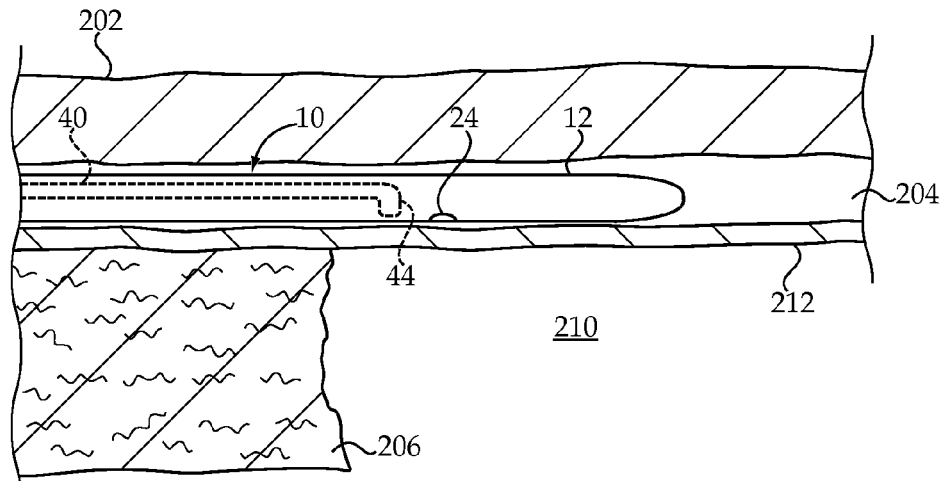
FIG. 8 is a side diagrammatic view at another stage of the procedure.
Figure 9:
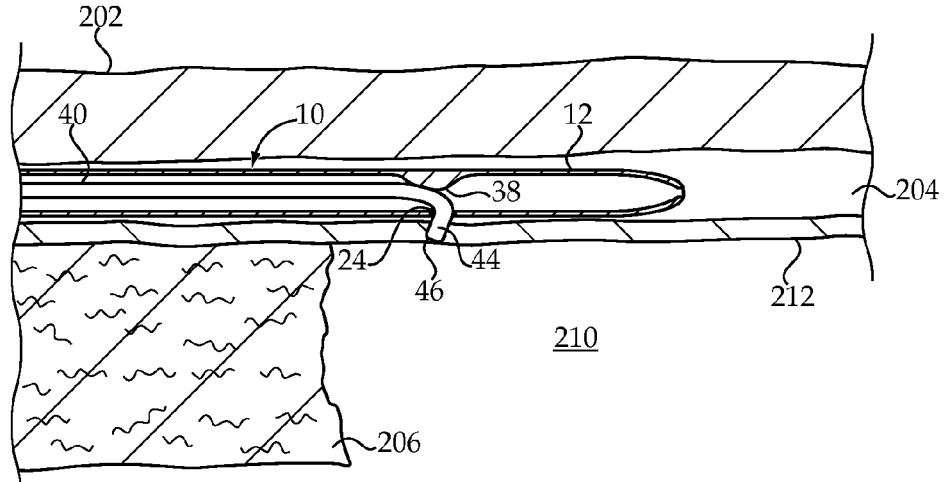
FIG. 9 is side diagrammatic view at yet another stage of the procedure.

In FIG. 8, tool 40 is shown in phantom and has been slid through catheter 12 such that distal end section 44 is nearly in axial alignment with side hole 24, which now faces down towards vascular wall 212 and true lumen 210. Referring also to FIG. 9, there is shown mechanism 10 where tool 40 has been slid to a position at which cutting tip 46 is in register with side hole 24, and then slid further such that cutting tip 46 punctures through vascular wall 212. Protrusion 38 is shown in catheter 12, and can be used to assist in urging cutting tip 46 out through side hole 34 to form the re-entry opening.

Figure 11:
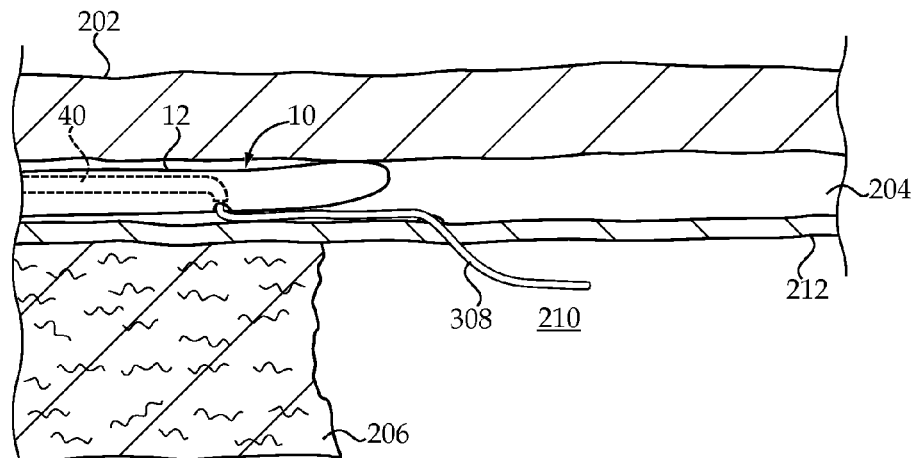
FIG. 11 is a side diagrammatic view at yet another stage of the procedure.
Figure 12:
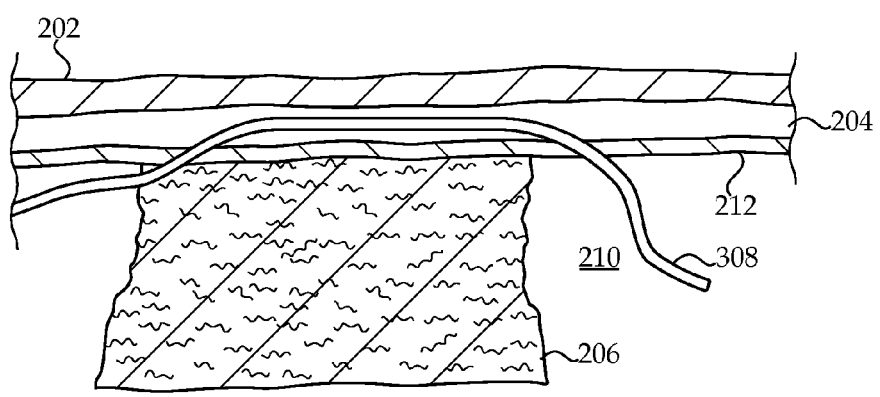
FIG. 12 is a side diagrammatic view at yet another stage of the procedure.

Referring also to FIG. 10, there is shown mechanism 10 where tool 40 has been fully advanced out of side hole 24, and another wire guide 308 has been advanced through tool 40 to enter true lumen 210. Referring now to FIG. 11, there is shown mechanism 10 where tool 40 has been withdrawn back into catheter 12, leaving wire 308 extending into true lumen 210, and catheter 12 has begun to be pulled back through subintimal space 204 for removal from the patient. In FIG. 11, catheter 12 has been entirely removed, and wire 308 passes subintimally past occlusion 206. From the state depicted in FIG. 12, wire 308 may be used as a guide for delivering other interventional tools such as a balloon, a stent, or another device, subintimally past occlusion 206 to create a conduit for restored blood flow through the vein or artery 202, and to enable accessing treatment locations further on.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. Other aspects, features and advantages will be apparent upon an examination of the attached drawings and appended claims.

What is claimed is:

1. A lumen reentry mechanism comprising:
    a catheter including an elongate tubular body for bypassing an area of stenosis in a vein or artery via a subintimal space, the elongate tubular body having a proximal body end and a distal body end, and defining a longitudinal axis, a passage extending longitudinally between the proximal and distal body ends, and a side hole connecting with the passage;
    the elongate tubular body further having a first and a second bead extending longitudinally between the proximal body end and the side hole, and projecting into the passage; and
    a piercing tool within the passage including an elongate proximal shaft section oriented substantially parallel to the longitudinal axis, and an attached distal end section oriented transverse to the elongate proximal shaft section and having a cutting tip configured to exit the side hole for forming a reentry opening from the subintimal space to a lumen of the vein or artery;
    the piercing tool being slidable within the passage from a first position to an advanced position at which the cutting tip is in axial alignment with the side hole, and the distal end section being trapped between the first and second beads such that contact between the cutting tip and the elongate tubular body is limited during the sliding of the piercing tool.

2. The mechanism of claim 1 wherein the piercing tool is in contact with at least one of the first and second beads and the cutting tip is positionable in register with the side hole via the trapping of the distal end section.

3. The mechanism of claim 2 wherein the piercing tool is at the first position, and wherein the first and second beads are oriented parallel to one another and each have a rounded shape.

4. The mechanism of claim 3 wherein the first and second beads each have a semi-circular cross-sectional shape in a section plane normal to the longitudinal axis.

5. The mechanism of claim 3 wherein a first longitudinal plane bisects the first bead, a second longitudinal plane bisects the second bead, and the cutting tip is positioned between the first and second longitudinal planes.

6. The mechanism of claim 5 wherein the longitudinal axis lies at an intersection of the first and second longitudinal planes, and the cutting tip is positioned within an angle defined by the first and second longitudinal planes and being less than 180°.

7. The mechanism of claim 6 wherein the angle is from about 120° to about 160°.

8. The mechanism of claim 6 wherein:
    the elongate tubular body has an outer diameter dimension of about 0.08 inches or less, and an inner diameter dimension of about 0.06 inches or less;
    the proximal shaft section defines a second longitudinal axis offset from the first longitudinal axis, and has an outer diameter dimension of about 0.03 inches or less; and
    the distal end section has a length from the proximal shaft section to the cutting tip of about 0.03 inches or less.

9. The mechanism of claim 8 wherein the proximal shaft and distal end sections are formed as one piece having a bend transitioning therebetween and defining a bend angle from about 45° to about 90°.

10. The mechanism of claim 5 further comprising a radiopaque stripe attached to the elongate tubular body and extending longitudinally between the proximal and distal body ends.

11. The mechanism of claim 10 further comprising a second radiopaque stripe parallel the first radiopaque stripe, and wherein the first and second radiopaque stripes are intersected by the first and second longitudinal planes, respectively.

12. A method of bypassing an area of stenosis in a vein or artery in a patient with a lumen reentry mechanism that includes a catheter with elongate tubular body for bypassing an area of stenosis in a vein or artery via a subintimal space, the elongate body having a proximal body end and a distal body end, and defining a longitudinal axis, a passage extending longitudinally between the proximal and distal body ends, and a side hole connecting with the passage; the elongate tubular body further having a first and a second bead extending longitudinally between the proximal body end and the side hole, and projecting into the passage; a piercing tool within the passage including an elongate proximal shaft section oriented substantially parallel to the longitudinal axis, and an attached distal end section oriented transverse to the elongate proximal shaft section and having a cutting tip configured to exit the side hole for forming a reentry opening from the subintimal space to a lumen of the vein or artery; and the piercing tool being slidable within the passage from a first position to an advanced position at which the cutting tip is in axial alignment with the side hole, and the distal end section being trapped between the first and second beads such that contact between the cutting tip and the elongate tubular body is limited during the sliding of the piercing tool, the method comprising the steps of:
    advancing the catheter defining the longitudinal axis past the area of stenosis via a subintimal space in the vein or artery;
    sliding the piercing tool having the elongate proximal shaft section and the transverse distal end section through the passage in the catheter to a position at which the cutting tip on the distal end section is in axial alignment with the side hole in the catheter connecting with the passage;
    trapping the distal end section, during sliding the piercing tool, between the first and the second longitudinally extending bead projecting into the passage, such that contact between the cutting tip and the catheter is limited; and
    forming a reentry opening from the subintimal space to a lumen of the vein or artery at least in part by advancing the distal end section out of the side hole such that the cutting tip pierces tissue forming a vascular wall defining the lumen.

13. The method of claim 12 further comprising a step of positioning the cutting tip in register with the side hole via the trapping of the distal end section.

14. The method of claim 13 wherein the step of trapping further includes contacting the distal end section with at least one of the first and second beads during the sliding of the piercing to form a line pattern of contact therewith.

15. The method of claim 14 wherein the step of sliding further includes sliding the piercing tool with the distal end section positioned at a fixed transverse orientation relative the elongate proximal shaft section.

16. The method of claim 15 wherein the step of sliding further includes sliding the piercing tool with the distal end section positioned between a first and a second radiopaque stripe of the catheter.

17. A lumen reentry mechanism comprising:
a catheter including an elongate tubular body for bypassing an area of stenosis in a vein or artery via a subintimal space, the elongate tubular body having a proximal and a distal body end, and defining a longitudinal axis, a passage extending longitudinally between the proximal and distal body ends, and a side hole connecting with the passage;
the elongate tubular body further having a first and a second bead extending longitudinally between the proximal body end and the side hole, and projecting into the passage; and
a piercing tool including an elongate proximal shaft section oriented substantially parallel to the longitudinal axis, and an attached distal end section oriented transverse to the elongate proximal shaft section and having a cutting tip configured to exit the side hole for forming a reentry opening from the subintimal space to a lumen of the vein or artery;
the piercing tool being slidable within the passage from a first position to an advanced position at which the cutting tip is in axial alignment with the side hole, and such that the distal end section is trapped during the sliding between the first and second beads to limit contact between the cutting tip and the elongate tubular body.

18. The mechanism of claim 17 wherein:
a first longitudinal plane bisects the first bead, and a second longitudinal plane bisects the second bead;
a first angle defined by the first and second longitudinal planes is less than 180°, and an opposite angle defined by the first and second longitudinal planes is greater than 180°; and
the longitudinal axis lies at an intersection of the first and second longitudinal planes.

19. The mechanism of claim 18 wherein:
the elongate tubular body has an outer diameter dimension of about 0.08 inches or less, and an inner diameter dimension of about 0.06 inches or less; and
the proximal shaft section has an outer diameter dimension of about 0.03 inches or less, and the distal end section has a length from the proximal shaft section to the cutting tip of about 0.03 inches or less.

20. The mechanism of claim 19 wherein the first and second beads each have a semi-circular cross-sectional shape in a section plane normal to the longitudinal axis and define an arc radius in the section plane of about 0.01 inches or less.

* * * * *